United States Patent [19]

Buchwald et al.

[11] Patent Number: 5,286,878
[45] Date of Patent: * Feb. 15, 1994

[54] CATALYTIC REDUCTION OF ORGANIC CARBONYLS

[75] Inventors: Stephen L. Buchwald, Somerville; Kristina A. Kreutzer, Cambridge, both of Mass.; Esther Spaltenstein, Raleigh, N.C.

[73] Assignee: Massachusetts Institute of Technology, Cambridge, Mass.

[*] Notice: The portion of the term of this patent subsequent to Jun. 15, 2010 has been disclaimed.

[21] Appl. No.: 616,892

[22] Filed: Nov. 21, 1990

[51] Int. Cl.$^5$ .................. C07P 207/06; C07P 207/20; C07C 33/22; C07C 29/132; C07C 29/147
[52] U.S. Cl. ..................... 548/577; 548/400; 548/578; 562/400; 568/814; 568/831
[58] Field of Search ............... 548/400, 577, 578; 562/400; 568/814, 831

[56] References Cited

U.S. PATENT DOCUMENTS 3,061,424 10/1962 Nitzsche et al. .................. 75/585
4,361,497 11/1982 Bold et al. ....................... 252/426

FOREIGN PATENT DOCUMENTS 2565234 6/1984 France .

OTHER PUBLICATIONS

Lipowitz, et al., "The Use of Polymethylhydrosiloxane (PMHS) as a Reducing Agent for Organic Compounds", Aldrichima Acta, vol. 6, p. 1, (1973).
Calas, Pure Appl. Chem., vol. 13, pp. 61 to 79 (1966).
"Dehydrogenative Coupling of Diarylsilanes", Organometallics 1989, 8, 1885-1893. Chang et al.
"Dehydrogenative Coupling of Heterocyclic Dihydrosilanes", Organometallics 1987, 6, 1595-1596. Corey et al.
"Cp$_2$TiPh$_2$-Catalyzed Dehydrogenative Coupling of Polyhydromonosilanes", Chemistry Letters, pp. 83-86, 1989, Nakano et al.
"Formation of Si-Si Bonds From Si-H Bonds in the Presence of Hydrosilation Catalysts", Organometallics 1987, 6, 1590-1591, Katherine A. Brown-Wensley.
The Corriu et al article, J. Organo. Met. Chem. 144 (1978) 155-164.
"Synthesis and Reactivity of Some t-butyl-disilanes and Digermanes", J. Organo. Met. Chem. 107 (1976) 23-32, Triplett et al.
"Preparation of New Types of Organosilicon Polymers, Effective Utilization of Disilane Fraction Produced in the Direct Synthesis of Methylchlorosilanes" Chemistry Letters, pp. 1883-1886, 1988, Wantanabe et al.
"Counterattack Reagents: Hexamethyldisilane and 1,2-Dimethyl-1,1,2,2-Tetrapheyldisilane in the Synthe- (List continued on next page.)

Primary Examiner—Floyd D. Higel
Attorney, Agent, or Firm—Thomas J. Engellenner; William C. Geary, III

[57] ABSTRACT

A process is provided whereby organic carbonyl substrates, including esters, ketones and amides, are reduced in a reaction with a silane reducing reagent and a catalyst. Effective catalysts broadly include those which consist of a group 4, 5 or 6 metal which either: a) is in less than its maximum oxidation state or is capable of being converted to a complex in less than its maximum oxidation state; and/or is a group 4, 5 or 6 metal hydride. Exemplary catalysts include titanium-containing catalysts such as (bis trimethylphosphine) titanocene, trimethyl phosphine adduct of a (hydrido) silyl complex of titanocene, titanocene dichloride and titanocene monochloride.

12 Claims, No Drawings

OTHER PUBLICATIONS sis of Polysilylated Hydrazines", Tetrahedron vol. 44, No. 13, pp. 4181–4196, (1988), Hwu et al.

"Chemistry of iridium carbonyl clusters. Preparation of $Ir_4(CO)_{12}$", J. Organo. Met. Chem., 331 (1987) 271–274, Della Pergola et al.

"Dimethylzirconocene–Catalyzed Polymerization of Alkylsilanes", Organometallics, 1989, 8, 2615–1618, Campbell et al.

"A Survey of Catalytic Activity of $n^5$–Cyclopentadienyl Complexes of Groups 4–6 and Uranium and Thorium for the Dehydrocoupling of Phenylsilane" Organometallics, 1989, 8, 1732–1736, Aitken et al.

Chuit et al., *Synthesis*, 1982, pp. 981–984.

Boyer et al., *Synthesis*, 1981, pp. 558–559.

Sato et al., *Tetrahedron Letters*, vol. 21, pp. 2175–2178, vo.s 21, pp. 2175–2178 (1980).

Nakano et al., *Chemistry Letters*, 1988, 481–484.

"Synthetic Strategy for the Coupling of the Calicheamicin Oligosaccharide with Aglycons: Synthesis of Dynemicin A–Calicheamicin Hybrid Structures" Nicolaou et al. (Agnew. Chem. Int. Ed. Engl. 30 (1991) No. 5. pp. 585–588).

CATALYTIC REDUCTION OF ORGANIC CARBONYLS

The U.S. Government has rights in this invention pursuant to contract Number N00014-88-K-0307 awarded by the Department of the Navy.

BACKGROUND OF THE INVENTION

The present invention relates to processes for catalytically reducing and/or transforming organic carbonyl compounds.

Methods currently are known for the catalytic reduction of organic carbonyls. Many such reduction reactions, such as those involving esters, ketones and amides, utilize lithium aluminum hydride or related species as a reducing reagent. Such reagents are quite pyrophoric and can ignite spontaneously upon contact with air or water. Moreover, lithium aluminum hydride typically is dispensed in a volatile liquid such as ether, thus compounding safety concerns. Aside from potential safety issues which surround the use of reducing reagents such as lithium aluminum hydride, their use can be costly as these compounds must be used in stoichiometric rather than catalytic quantities. A further disadvantage of reactions which use lithium aluminum hydride as a reducing agent is that they yield an aluminum salt as a by-product, from which the desired end product is often difficult to isolate.

Reactions which reduce organic carbonyls, such as esters, ketones and amides, often are commercially quite significant, as they can be used in the large scale preparation of pharmaceuticals and specialty chemicals. Thus, the safety and economy of the reduction reactions are important considerations. Accordingly, it would be advantageous to provide safer and more economical processes for reducing organic carbonyl compounds.

It is thus an object of the invention to provide a safer and more economical process for reducing organic carbonyl compounds such as esters, ketones and amides. Another object is to provide such a reaction where the end product of the reaction is effectively and conveniently isolated. Other objects will be apparent upon reading the disclosure which follows.

SUMMARY OF THE INVENTION

The invention provides a relatively safe and effective catalytic process for conveniently reducing organic carbonyl compounds, including esters, ketones and amides. The applicability of this Process to the manufacture of pharmaceuticals and specialty chemicals will be appreciated by those having ordinary skill in the art. Among the organic carbonyls which can be reduced by the processes of this invention are esters, ketones and amides. Esters and ketones can be reduced to alcohols, while amides can be reduced to amines. In some instances lactones can be reduced to lactols or diols. In another embodiment of the invention, tertiary amides can be reduced to yield enamine compounds.

Generally, the process of the invention involves first generating an active species of an effective reduction catalyst which is used in the reaction. In one embodiment, the catalyst is a titanium-containing catalyst, however, other catalysts may be used as well. A stoichiometric amount of a silane reducing reagent is then combined with a catalytic amount (i.e., about 3 to 10 percent by mole) of the catalyst. The desired organic carbonyl substrate is then allowed to react with the silane reagent in the presence of the catalyst. The reduction of esters and ketones by this reaction yields a silicon-containing intermediate. Silicon is cleaved from the intermediate by conventional techniques, after quenching of the catalyst, to yield a crude end product in a more reduced form than the starting compound. The end product may then be purified by known techniques. Reduction reactions in which the carbonyl substrate is an amide do not require a silicon cleavage step. Following the reduction of amide one need only perform conventional separation and purification techniques to yield the desired end product.

Those skilled in the art will appreciate that the term "catalyst" is used herein to encompass both catalysts and precatalysts.

DETAILED DESCRIPTION OF THE INVENTION

The process of the invention can be used to catalytically reduce organic carbonyl compounds such as esters, ketones and amides. Esters and ketones can be reduced to alcohols, and where the ester is a lactone, it can be reduced to either a lactol or a diol. Amides can be reduced to amines, or in one embodiment, to enamines. One important feature of the process of the invention is that it utilizes relatively inexpensive and safe catalysts and reducing reagents.

The basic steps of the invention involve first generating an active species of an effective catalyst which, depending upon the identity of the catalyst, may be dispensed in an organic solvent such as tetrahydrofuran, ether, toluene, benzene, hexane, or the like. Preferably, this mixture is maintained in an atmosphere of an inert gas such as argon or nitrogen within which the reduction reaction takes place. In some instances, especially where certain titanium-containing catalysts are used as explained below in more detail, the catalyst is activated by dissolving the catalyst in a solvent together with an alkylating agent.

Once the active catalyst is formed, it is mixed with a silane reducing reagent which provides the source of hydride ion for the reduction reaction. Usually, the catalyst-solvent mixture is maintained at a relatively low temperature (e.g., between about $-60°$ C. to $-78°$ C.) until it is mixed with the silane. Thereafter, the mixture may be allowed to warm to between about 0° C. and room temperature. It is noted, however, that the catalyst may also be generated at room temperature. The organic carbonyl substrate is then reacted, at a temperature between about room temperature and 60° C., with the silane reagent in the presence of the activated catalyst. Typically, the reaction requires from about 15 minutes to 3 hours to complete. The reaction can be terminated by deactivating the catalyst through exposure to air.

This reaction, when performed with esters and ketones, yields a silicon-containing intermediate compound. The silicon may be cleaved from the intermediate by a variety of known extraction techniques to isolate the desired end product of the reduction reaction. For example, silicon cleavage may be effected by treatment with ethanolic or aqueous solutions of hydrochloric acid or sodium hydroxide. Subsequently, separation and drying techniques can be utilized to recover the crude product, which can then be purified by a conventional technique such as chromatography. The reduction of amides to amines or enamines does not require a silicon cleavage step. However, separation and purification techniques generally must be effected to recover the desired end product.

The invention is generally applicable to the reduction of organic carbonyl substrates. Exemplary carbonyl compounds include acyclic and cyclic esters, ketones and amides. The invention is also potentially applicable to the reduction of compounds such as aldehydes, acids, acid chlorides and thioesters.

A variety of catalysts can be used effectively in the reduction reactions of the present invention. Exemplary catalysts broadly include those which consist of a group 4, 5 or 6 metal which either: a) is in less than its maximum oxidation state or is capable of being converted to a complex in less than its maximum oxidation state; and/or b) is a metal hydride. Examples of group 4, 5 and 6 metals which may be useful in the present invention include titanium, vanadium and chromium. Preferred catalysts are titanium-containing catalysts such as bis (trimethylphosphine) titanocene, trimethylphosphine adduct of a (hydrido) silyl complex of titanocene, titanocene monochloride and titanocene dichloride. Of the above identified titanium-containing catalysts, titanocene dichloride and titanocene monochloride are activated by reaction with an alkylating or reducing agent. Examples of other suitable titanium-containing catalysts include compounds having the following general structures: L(L')(L'')Ti; L(L')(L'')(L''')Ti; L(L')Ti-X; L(L')(L'')Ti-X; L(L')TiX$_2$; and L(L')TiH, where X is a halogen, and where L, L', L'' and L''' can be some combination of —OR, —SR, —NR(R'), where R and R' may be an alkyl or aryl group and may be different or the same, or a cyclopentadienyl group (hereinafter "Cp") having the formula

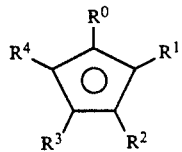

where $R^0$, $R^1$, $R^2$, $R^3$ and $R^4$ may be hydrogen, alkyl or aryl groups in any combination and may all be the same or different. More specific examples of such compounds include titanocene alkoxides, titanocene aryloxides, titanocene (III) hydrides, titanocene (aryloxy) chlorides, and titanocene (alkoxy) chlorides.

As noted above, one preferred titanium-containing catalyst is bis (trimethylphosphine) titanocene, having the formula

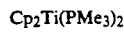   (I)

Wherein Cp represents a $\eta^5$-cyclopentadienyl group and Me represents a methyl group. Another preferred titanium-containing catalyst is trimethylphosphine adduct of a (hydrido) silyl complex of titanocene which has the general formula

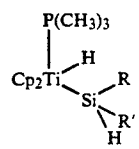   (II)

wherein Cp represents a $\eta^5$-cyclopentadienyl group and R and R' each represent an aryl or an alkyl group and may be the same or different.

The catalytic species identified above by formulas I and II are self-activating and should be maintained in solution with an organic solvent and maintained at a relatively low temperature (0° C. to 80° C.) in the absence of air and excess moisture.

One of the more preferred titanium-containing catalysts is titanocene dichloride which is represented by the formula Cp$_2$TiCl$_2$ wherein Cp represents a $\eta^5$-cyclopentadienyl group. Alternatively, titanocene monochloride (Cp$_2$TiCl) may be used as a catalyst as well. The titanocene dichloride and titanocene monochloride catalysts must be activated by reaction with an alkylating agent, preferably in an organic solvent. Suitable alkylating agents are known to those skilled in the art and generally include organometallic compounds. Examples of such compounds include alkyl magnesium halides, alkyl lithium compounds and alkyl aluminum compounds. Particularly preferred alkylating agents include n-pentyl magnesium bromide and n-butyl lithium. Preferably, about 100 to 200% by mole of the alkylating agent, relative to the catalyst, should be reacted with the catalyst in order for activation to occur. More preferably, titanocene dichloride requires about 200% by mole of alkylating agent while titanocene monochloride requires about 100% by mole. The activation of such catalysts by reaction with an alkylating agent is further described and illustrated in the examples.

One skilled in the art will appreciate that a variety of solvents can be used with these catalysts. One general requirement of a suitable solvent is that the catalyst must be completely or partially soluble within the solvent. Complete solubility is not required as there need only be enough catalyst present in the solution to facilitate a reaction. Exemplary solvents include tetrahydrofuran, toluene, benzene, hexane, ether and the like. An additional advantage of the invention is that the substrate may be present in the organic solvent at relatively high concentrations (e.g., about 1M), thus enabling smaller reactors to be used and less waste solvent to be generated. It is noted that no solvent other than the silane itself may be required.

As noted above, the reducing reagent preferred in the present processes is a silane compound which must be capable of supplying a hydride ion during the reduction reaction. Exemplary silane compounds which may be used in these processes are represented by the formulas shown below.

R(R')SiH$_2$   (III)

RSiH$_3$   (IV)

RO(R'O)SiH$_2$   (V)

R(R')SiH$_2$   (III)

RSiH$_3$   (IV)

RO(R'O)SiH$_2$   (V)

-continued

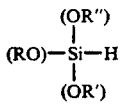

where R, R' and R" represent alkyl or aryl groups and may be the same or different. Specific examples of suitable silane reducing reagents include diphenyl silane, phenyl silane, diethyl silane, dimethyl silane and triethoxy silane.

Preferably, the silane reducing reagent is used in an amount ranging from about 100 to about 300% by mole as compared to the amount of the substrate.

In an alternative embodiment, amides may be reduced to cyclic or acyclic enamine compounds having the general formula

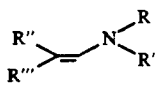

where R, R', R" and R'" represent hydrogen, alkyl or aryl groups. The enamines produced may also include cyclic compounds where R and R", shown above in formula VII, are connected. It is believed that in this reaction the enamines may actually be isolable intermediates in the reduction reactions of heterocyclic amides to heterocyclic amines. An example of a reaction which may be used to reduce amides to enamines utilizes (bis trimethyl phosphine) titanocene as a catalyst. Approximately 10 percent by mole of this catalyst is dissolved in 650 $\mu$L of $C_6D_6$. Diphenyl silane and then the desired amide substrate are added to the catalyst solution. This reaction yields a variable ratio of amine and enamine, depending upon the amide substrate and reaction conditions which are used. The addition of a hydrogen acceptor can lead to the generation of additional enamine.

The invention is further illustrated by the examples which follow.

EXAMPLE I

Reduction of ethyl cyclohexylcarboxylate to cyclohexylmethanol

To a dry Schlenk tube under argon was added 37 mg of titanocene dichloride (0.15 mmol) and 2 mL of tetrahydrofuran. The slurry was cooled to about $-78°$ C. in a dry ice/acetone bath, and a 1.6M hexane solution of n-butyl lithium (188 $\mu$L, 0.3 mmol) was added. The reaction mixture changed color from red to dark brown. After stirring for 15 minutes, 1.4 mL of triethoxysilane (7.5 mmol) and 468 mg of ethyl cyclohexylacetate (3.0 mmol) were added and the reaction mixture was allowed to warm to room temperature. After 1 hour, the catalyst was deactivated by exposure to air until the color changed from dark brown to yellow. Next, 10 mL of tetrahydrofuran and 0.5 mL of concentrated HCl were added. After stirring for 2 hours, the mixture was added to a water/ether mixture (150 mL each), shaken vigorously, and the layers were then separated. The aqueous layer was extracted with ether (2×50 mL), the combined organic extracts were washed with brine, dried over MgSO$_4$, filtered, and concentrated by rotary evaporation. The crude product was purified by flash chromatography (ether:hexane=2:3), which afforded 274 mg (80% yield) of cyclohexylmethanol.

EXAMPLE II-A

Reduction of ethyl 2-phenylethanoate to phenethyl alcohol

To a dry Schlenk tube under argon was added 50 mg of titanocene dichloride (0.2 mmol) and 2 mL of tetrahydrofuran. The slurry was cooled to $-78°$ C. in a dry ice/acetone bath and 200 $\mu$L of a 2M ether solution of pentylmagnesium bromide (0.4 mmol) was added. After stirring for 15 minutes, 930 $\mu$L of diphenylsilane (5.0 mmol) was added and the reaction mixture was allowed to warm to 0° C. Next 637 $\mu$L of ethyl 2-phenylethanoate (4.0 mmol) was then added and the reaction mixture was allowed to warm to room temperature. After 2 hours, an additional 200 $\mu$L of diphenylsilane was added and the reaction was stirred for 1.5 hours. The catalyst was then quenched by exposure to air until the color changed from dark brown to yellow. 5 mL of tetrahydrofuran and 15 mL of 1N NaOH in MeOH solution were then added. After stirring for 2 hours, the mixture was added to a brine/hexane mixture (150 mL each), shaken vigorously, and the layers were then separated. The aqueous layer was extracted with hexane (2×50 mL), the combined organic extracts were dried over MgSO$_4$, filtered, and concentrated by rotary evaporation. The crude product was purified by flash chromatography (ether:hexane=3:7), which afforded 397 mg (81% yield) of phenethyl alcohol.

EXAMPLE II-B

Alternative method of reducing ethyl 2-phenylethanoate to phenethyl alcohol

To a dry Schlenk tube under argon was added 50 mg of titanocene dichloride (0.2 mmol) and 2 mL of tetrahydrofuran. The slurry was cooled to $-78°$ C. in a dry ice/acetone bath and 250 $\mu$L of a 1.6M hexane solution of n-butyl lithium. (0.4 mmol) was added. After stirring for 15 minutes, 1.8 mL of triethoxysilane (10 mmol was added, followed by 500 $\mu$L ethyl 2-phenylethanoate (3.0 mmol), and the reaction mixture was allowed to warm to room temperature. The reaction mixture bubbled vigorously. When the bubbles subsided, the reaction mixture began to warm rapidly, causing tetrahydrofuran to begin refluxing. When the mixture cooled back to room temperature, the catalyst was quenched by exposure to air until the color changed from dark brown to yellow. Next, 5 mL of tetrahydrofuran, 15 mL of EtOH, and 0.6 g of NaOH (15 mmol) were then added. After stirring for 2 hours, the mixture was added to a water/ether mixture (150 mL each), shaken vigorously, and the layers were then separated. The aqueous layer was extracted with ether (2×50 mL), the combined organic extracts were dried over MgSO$_4$, filtered, and concentrated by rotary evaporation. The crude product was purified by flash Chromatography (ether:hexane=1:1), which afforded 300 mg (82% yield) of phenethyl alcohol.

EXAMPLE III

Reduction of ethyl 3-phenylpropionate to phenpropyl alcohol

To a dry Schlenk tube under argon was added 50 mg of titanocene dichloride (0.2 mmol) and 2 mL of tetrahydrofuran. The slurry was cooled to $-78°$ C. in a dry ice/ acetone bath and a 2.50 $\mu$L of a 1.6M hexane solution of n-butyl lithium (0.4 mmol) was added. After stirring for 15 minutes, 930 μL diphenylsilane (5.0 mmol) was added and the reaction mixture was allowed to warm to 0° C. Then 712 μl of ethyl 3-phenylpropionate (4.0 mmol) was then added, and the reaction mixture was allowed to warm to room temperature. After 0.5 hour, the catalyst was deactivated by exposure to air until the color changed from dark brown to yellow. 5 mL of tetrahydrofuran and 15 mL of a solution of 1N NaOH in MeOH were then added. After stirring for 2 hours, the mixture was added to a brine/hexane mixture (150 mL each), shaken vigorously, and the layers were then separated. The aqueous layer was extracted with hexane twice (2×50 mL), the combined organic extracts were dried over MgSO$_4$, filtered, and concentrated by rotary evaporation. The crude product was purified by flash chromatography (ether:hexane=2:3), which afforded 446 mg (82% yield) of 3-phenpropyl alcohol.

EXAMPLE IV

Reduction of N-phenylpyrrolidinone to N-phenylpyrrolidine

Titanocene dichloride (0.55 g, 2.2 mmol) was dissolved in 15 mL of tetrahydrofuran in a nitrogen atmosphere and the solution was cooled to −78° C. Next, 2.8 mL of n-butyl lithium (1.6M) was added to the solution. The reaction mixture was stirred for 15 min and then 9.0 mL of diphenylsilane (49 mmol) was added. The mixture was warmed to room temperature and 3.6 g of N-phenylpyrrolidinone (22 mmol) was added to the black solution, which began bubbling and became warm after 1-2 minutes. The reaction mixture was stirred overnight at room temperature and then heated to 55° C. for 1 hour. The solution was then poured into 50 mL of ethyl ether and extracted with 1M HCl (5×50 mL). The aqueous layer was washed with (50 mL) of ethyl ether and a saturated solution of aqueous NaHCO$_3$ was added to the aqueous layer until it became basic to pH paper. The solution was then extracted with ethyl ether (5×50 mL). An emulsion formed and a 50 mL of a saturated NaCl solution was added to the ether and emulsion layer. The ether was decanted away from the emulsion, which was extracted with (75 mL) of ethyl ether. The ether solution was then dried over MgSO$_4$, filtered, and evaporated in vacuo. A yellow-orange oil (3.5 g, 86% pure by GC, 93% crude yield) was obtained. The $^1$H NMR spectrum shows the impurity was siloxane byproduct from the reaction. The product was again dissolved in ether, extracted into aqueous HCl, and extracted back into ether after neutralizing the acid with NaHCO$_3$. After drying over MgSO$_4$, filtration, and concentration in vacuo, 2.3 g of N-phenylpyrrolidinone as a yellow oil was isolated (72% isolated yield).

EXAMPLE V

Reduction of N-benzylpyrrolidinone to N-benzylpyrrolidine

Titanocene dichloride (0.28 g, 1.1 mmol) was dissolved in (15 mL) of tetrahydrofuran in a nitrogen atmosphere and the reaction mixture was cooled to −78° C., and 2.4 mL of a 1.6M solution of n-butyl lithium in hexane was added. The reaction mixture was stirred for 15 min and then 4.5 mL diphenylsilane (24 mmol) was added. After warming the reaction mixture to room temperature, 1.8 g of N-benzylpyrrolidinone (11 mmol) was added to the black solution, which began bubbling and became warm (i.e., about 30° C.) after 1–2 min. The reaction mixture was stirred overnight at room temperature and then heated to 55° C. for 1 hour. The solution was then poured into 50 mL of ethyl ether and extracted with 1 M HCl (3×50 mL). The aqueous layer was washed with ether (2×25 mL) and then neutralized with a 5 M NaOH solution so that the aqueous layer was basic to pH paper. The product was extracted into ether (3×50 mL) and the emulsion that formed was also extracted with ether (50 mL). The combined ether extracts were dried over MgSO$_4$, filtered, and concentrated in vacuo. N-benzylpyrrolidine was isolated as a yellow oil (1.58 g of 95% pure material, 84% yield).

EXAMPLE VI

Reduction of acetophenone to sec - phenethyl alcohol

To a dry Schlenk tube under argon was added 37.6 mg (0.15 mmol) of a titanocene dichloride and 3 mL of tetrahydrofuran. The slurry was cooled to −78° C. and a 1.64 M hexane solution of n-butyl lithium (190 μL, 0.3 mmol) was added. After stirring for 15 minutes, triethoxysilane (140 μL, 0.75 mmol) was added. The black mixture was allowed to warm to 0° C., then acetophenone (350 μL, 3.0 mmol), followed by more triethoxysilane (700 μL, 3.75 mmol) were added. The reaction mixture was allowed to stir for 6 hours at room temperature. The Schlenk tube was opened to air and 5 mL of water were added and allowed to stir at room temperature for 1 hour. A solution of 5 M NaOH (1 mL) was added and allowed to stir. When the reaction mixture had turned to a white slurry additional 5M NaOH and 5 mL of tetrahydrofuran were added. After stirring for 1 hour, the mixture was added to a water/ether mixture (150 mL each), shaken vigorously, and the layers were then separated. The aqueous layer was extracted with ether (2×50 mL) and the combined organic extracts were dried over MgSO$_4$, filtered, and concentrated by rotary evaporation. The crude product was purified by flash chromatography (ether:hexane=1:2), which yielded 295 mg (80% yield) of sec-phenethyl alcohol.

With respect to the above examples, it is noted that the reactions were run under an atmosphere of either nitrogen or argon. Further, the tetrahydrofuran, diethyl ether and benzene used in the examples were distilled under argon from sodium/benzophenone ketyl before use. The titanocene dichloride was purchased from Boulder Scientific Inc. of Mead Colorado, and was used without further purification. All other reagents were available from commercial sources and were used without further purification unless noted otherwise.

The above examples are intended to be illustrative of the invention and should not be read to limit the invention to the specific reduction reactions provided in the examples. One skilled in the art will readily appreciate that the invention is applicable to a variety of reduction reactions in which the substrate is an ester (acyclic or cyclic), a ketone or an amide, and that a variety of catalysts may be used in these reduction reactions.

What is claimed is:

1. A process for catalytically reducing organic carbonyl compounds, comprising the steps of:
    providing a catalytic amount of an active species of a catalyst selected from the group consisting of a group 4, 5 or 6 metal which is capable of being converted to a complex in less than its maximum oxidation state, a complex of a group 4, 5 or 6 metal in less than its maximum oxidation state, and a group 4, 5 or 6 metal hydride;

adding to the catalyst a stoichiometric amount of a silane compound able to contribute a hydride ion during the reduction reaction;

reacting an organic carbonyl substrate selected from the group consisting of acyclic esters, cyclic esters, and amides with the silane compound in the presence of said catalyst at a temperature of between about room temperature and 60° C.; and recovering and purifying the reaction product.

2. The process of claim 1 wherein the said catalyst is a titanium-containing catalyst selected from the group consisting of (bis trimethylphosphine) titanocene, titanocene monochloride, titanocene dichloride and trimethylphosphine adduct of a (hydrido) silyl complex of titanocene having the structure:

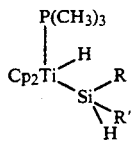

wherein Cp represents a $\eta^5$-cyclopentadienyl group, and R and R' represent aryl groups, alkyl groups or combinations thereof.

3. The process of claim 1 wherein said catalyst is a titanium-containing catalyst selected from the group consisting of L(L')(L'')Ti, L(L')(L'')Ti-X, L(L')(L'')(L''')Ti, L(L')Ti-X, L(L')Ti-$X_2$ and L(L')Ti-H where X is a halogen, and where L, L', L'' and L''' can be —OR, —SR, —NR(R') or a cyclopentadienyl group of the structure

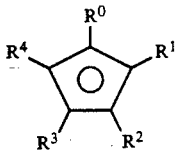

where R and R' can be an alkyl or aryl group, and $R^0$, $R^1$, $R^2$, $R^3$ and $R^4$ can be hydrogen, an alkyl group or an aryl group.

4. The process of claim 3 wherein active species of titanium monochloride and titanium dichloride catalysts are generated by reaction with an organometallic alkylating agent.

5. The process of claim 5 wherein the organometallic alkylating agent is selected from the group consisting of n-butyllithium and n-pentylmagnesium bromide.

6. The process of claim 1 wherein the silane compound is selected from the group consisting of diphenylsilane, phenylsilane, diethylsilane, dimethylsilane and triethoxysilane.

7. The process of claim 1 wherein the catalyst is present in an amount ranging between about 3 and 10 percent by mole.

8. The process of claim 6 wherein an ester substrate is reduced to an alcohol, a lactol or a diol.

9. The process of claim 9 wherein following the step of reacting the substrate with the silane compound in the presence of the catalyst, the process further comprises the step of cleaving silicon from the resulting reaction product.

10. The process of claim 7 wherein a ketone substrate is reduced to an alcohol.

11. The process of claim 11 wherein following the step of reacting the substrate with the silane compound in the presence of the catalysts, the process further comprises the step of cleaving silicon from the resulting reaction product.

12. The process of claim 1 wherein an amide substrate is reduced to an amine, an enamine or a mixture thereof.

* * * * *